United States Patent [19]

Bond

[11] 4,147,064

[45] Apr. 3, 1979

[54] TESTING OF MATERIALS WITH STRESS WAVES

[75] Inventor: Robert Bond, Lichfield, England

[73] Assignee: Dunlop Limited, London, England

[21] Appl. No.: 782,395

[22] Filed: Mar. 29, 1977

[30] Foreign Application Priority Data

Apr. 7, 1976 [GB] United Kingdom ............... 14209/76

[51] Int. Cl.² .............................................. G01N 29/00
[52] U.S. Cl. .......................................... 73/596; 73/597
[58] Field of Search .................. 73/67.1, 67.2, 67.5 R, 73/67.6, 596–600, 618

[56] References Cited

U.S. PATENT DOCUMENTS

| | | |
|---|---|---|
| 2,483,821 | 10/1949 | Firestone ............................. 73/67.6 |
| 2,503,400 | 4/1950 | Mason ............................... 73/67.5 X |
| 2,667,063 | 1/1954 | Cunningham ......................... 73/598 |
| 3,447,278 | 11/1969 | Lynnworth ....................... 73/67.6 X |
| 3,664,180 | 5/1972 | McDonald et al. .................. 73/67.6 |
| 3,690,155 | 9/1972 | Eichler .............................. 73/67.5 R |

*Primary Examiner*—James J. Gill
*Attorney, Agent, or Firm*—Stevens, Davis, Miller & Mosher

[57] ABSTRACT

A sample of material is tested to determine its elastic properties by generating a stress wave from a first transducer and comparing the stress wave received by a second transducer positioned on the opposite side of the sample to the first transducer. The phase shift and attenuation are used to calculate the elastic properties of the material.

12 Claims, 1 Drawing Figure

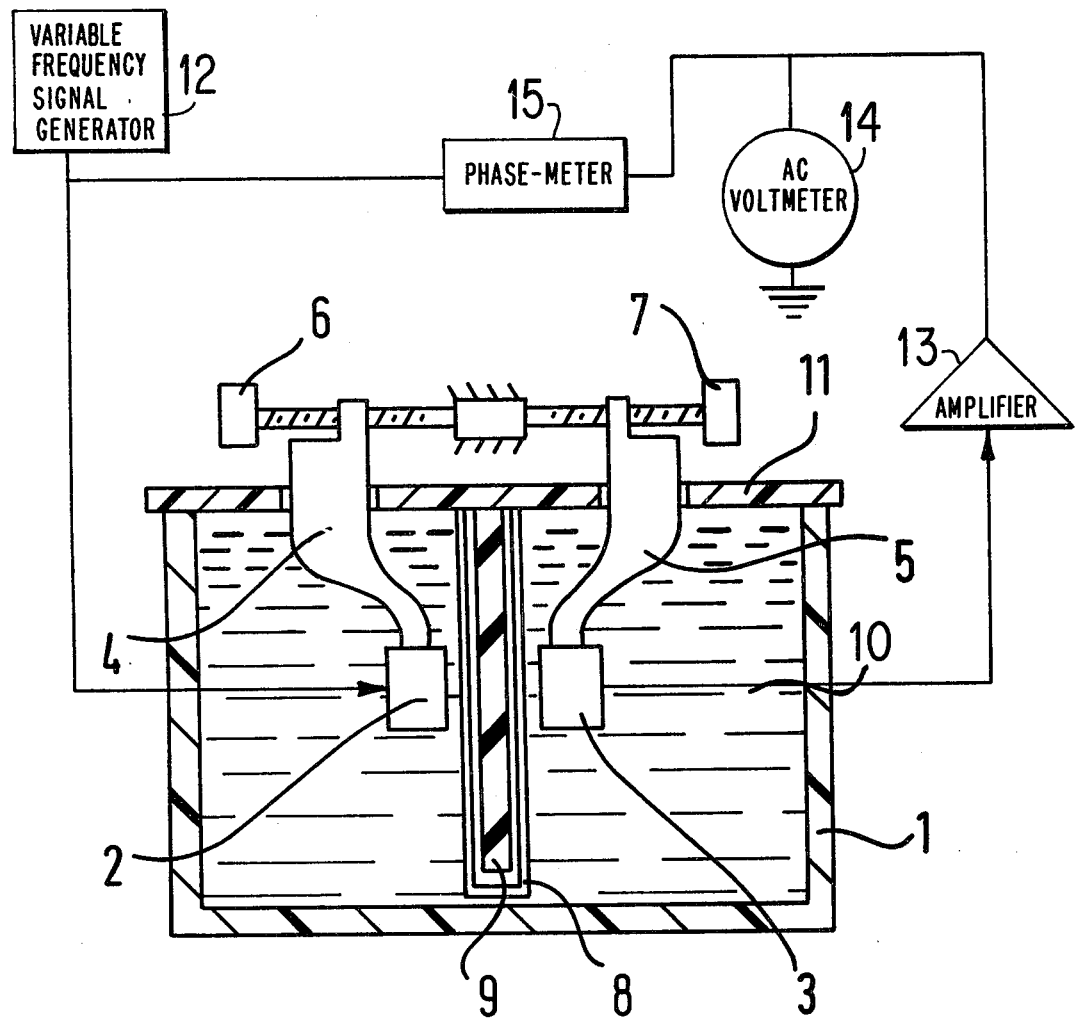

TESTING OF MATERIALS WITH STRESS WAVES

This invention is concerned with the testing of materials, and is particularly concerned with methods of evaluating elastic properties by the transmission of longitudinal stress waves.

According to the present invention there is provided apparatus for determining elastic properties of materials comprising a tank containing a fluid, a first transducer for generating stress waves, a second transducer for detecting and receiving waves from the first transducer, said first and second transducers being aligned on a common axis support means for detachably supporting a sample of material within said tank, between said first and second transducers such that the surface of said sample is perpendicular to said common axis and means for comparing properties of the waves generated by said first transducer and the waves received by said second transducer.

According also to the present invention a method of measuring the elastic properties of a material at two frequencies comprising the steps of:
  (i) arranging first and second transducers in spaced relationship such that a dilatational stress wave originating from the first transducer may be received by the second transducer
  (ii) adjusting the second transducer such that the signal received is a maximum
  (iii) positioning between said transducers a sample of the material to be tested
  (iv) comparing the stress wave received at the second transducer with that transmitted by the first transducer and calculating the elastic properties
  (v) repeating steps (i)–(iv) for a second frequency.

In this specification "elastic modulus" of a material is to be taken to mean the modulus applicable to stress-wave propagation—i.e.

$$K + \frac{4G}{3}$$

where K is the bulk modulus and G the shear modulus of the material.

The method may be used for testing at any number of different frequencies, although it will be appreciated that the range of possible frequencies will depend on the quality factor Q of the crystals used in the transducers. Thus, if testing over a wide range of frequencies is required, crystals of very low Q are necessary to ensure a generally acceptable sensitivity of measurement. Preferably the Q of the crystals is less than 200, more preferably less than 100.

The method of the invention is found to be particularly useful for the testing of rubber, but is not limited thereto. Preferably a fluid is used to act as a transmitting medium between the transmitting crystal and the sample, and between the sample and receiving crystal. It is preferable that the fluid has an acoustic impedance (i.e. density x wave velocity) similar to that of the material to be tested so as to minimize reflection of stress-waves at the sample/fluid interfaces. For use with rubber, water is a suitable transmitting fluid: where higher temperature operation is required, castor oil may be used, whilst at low temperatures, i.e. down to −20° C., a mixture of water and ethylene glycol is found to be satisfactory. In practice it is found desirable to immerse the sample to be tested in the fluid for a period before testing to ensure the absence of air bubbles which might cause spurious reflections.

Step (iv) may be achieved by comparing the results obtained from the apparatus when the sample is in position with those obtained in the absence thereof, either on the same apparatus, or using a second apparatus to permit direct comparison. One test without a sample may conveniently be used as a single calibration for a number of measurements or samples.

The invention will now be further described by way of example only, with reference to the accompanying drawing which shows a testing apparatus suitable for performing the method of the invention. The apparatus is designed to test rubber samples over a frequency range of 40 kHz to 1 MHz and over a temperature range of 20° C. to 150° C.

The apparatus comprises a tank 1, constructed of plastics material so as to minimize internal reflection of stress waves. Positioned in the tank are two crystal transducers: an exciter crystal 2 and pickup crystal 3, each crystal being mounted on a bracket 4, 5 provided with screw adjusters 6, 7 for adjustment of the crystal spacing. The crystals are identical, having a Q of 80 and a resonant frequency of 1.8 MHz. Located between the crystals are guides 8 for location of a sample of the rubber to be tested. In use, the tank 1 is filled with castor oil 10 as a transmitting fluid, and is fitted with a lid 11, of plastics material.

In operation the exciter crystal 2 is energized by a signal generator 12 at the desired frequency, and continuously transmits stress waves through the transmitting fluid, through the sample 9 (if present), and through further transmitting fluid, when they are received by the pickup crystal 3. Castor Oil is chosen as the transmitting fluid as it will operate satisfactorily over the required temperature range, and has an acoustic impedance similar to that of rubber so that no significant reflections at the fluid/sample interfaces occur. However, reflection will occur when a stress wave impinges upon the pickup crystal 3 and a reflected wave will travel from the crystal 3 back through the sample to the exciter crystal, at which point a further reflection occurs. It can readily be seen that an infinite number of reflections occur, each reflected wave being progressively weaker due to transmission and reflection losses. Interaction of the original and successive reflected waves produces a standing wave pattern characterised by spaced-apart points (nodes and antinodes) of minimum and maximum peak stress between the two crystals. Analysis of reflections and standing waves is a well-known problem in wave theory.

The preferred method of testing involves measuring the degree of phase shift and attenuation, of the receive signal due to the presence of the sample.

One means of carrying out the method will now be described. First, the apparatus is operated at the desired frequency and temperature without a sample—i.e. with transmitting fluid filling the space normally occupied by the sample. The pickup crystal 3 is connected, via a suitable amplifier 13, to an AC voltmeter 14 and a phase-meter 15 (meaning the phase relative to the signal generator output as an arbitrary datum). The crystal spacing is adjusted so that the output from the pickup crystal is a maximum—i.e. so that the pickup crystal is located at a standing wave antinode. This is a convenient method of ensuring that the position of the crystal is known in relation to the standing wave pattern. At low frequencies, e.g. below 50 kHz, the waves have a relatively long wavelength and, if movement of the crystals is limited it may not be possible to locate the receiving crystal at an antinode. In this situation the crystal is adjusted to a known position in relation to the standing wave pattern and a suitable correction made in evaluation of the results.

The sample 9 (e.g. of rubber) is then inserted in the guides 8.

Whilst in principle the method is applicable to any size of sample, for accurate results to be obtained the sample should extend in the transverse direction sufficiently to avoid any direct transmission of waves from the exciter crystal to the receiving crystal without passing through the sample. The thickness of the sample (i.e. measured in a direction parallel to a line joining the crystals) is limited in practice only by the sensitivity of the apparatus. It should be noted, however, that it is not electrically possible to identify phase-shifts in excess of 360°, and it is therefore desirable to make two or more phase-shift measurements on samples of different thicknesses to ensure that, for example, a measurement of 30° is not erroneously obtained where the true figure is 390°. By way of example, the apparatus described has been satisfactorily used with three sample sizes:

(a) 170 mm × 70 mm × 4 mm
(b) 170 mm × 70 mm × 6 mm
(c) 170 mm × 70 mm × 12 mm

Due to the different wave velocity of the rubber as compared with the transmitting fluid, the phase of the received signal will change, and this phase change can be read by the operator from the phase-meter: alternatively, of course, it could be recorded automatically. A change in the amplitude of the received signal will also occur. This is due to two factors: a change in the standing wave pattern, due to the aforementioned phase shift, so that the pickup crystal 3 is no longer located at an antinode; and the signal loss in the sample. There are two ways of separating the desired information: (i) to readjust the crystal spacing to correct for the phase shift and then measure the signal amplitude, or (ii) to measure the signal amplitude without readjustment and correct for the phase shift in later calculation. In cases where the final results are derived using a computer, the latter method is preferable as it simplifies the testing procedure. Using the latter method, the modulus of the sample may be found from the phase-shift from $$\left(K + \frac{4G}{3}\right) = \rho \left\{ \frac{2\pi f d\, v_1}{2\pi f d - v_1 \tan^{-1}\left[\left(\frac{1+\beta}{1-\beta}\right)\tan\left(\gamma + \frac{\alpha_1 v_1}{2\pi f}\right)\right]} \right\}^2$$

where
f is the frequency of operation (Hz)
d is the sample thickness (m)
$v_1$ is the signal velocity in the transmitting fluid $(ms^{-1})$
$\beta$ is the reflection coefficient at the fluid/crystal interfaces (determined experimentally from the initial standing wave ratio)
$\alpha_1$ is the attenuation of the signal in the transmitting fluid$(m^{-1})$
$\gamma$ is the phase shift
$\rho$ is the density of the material (kg $m^{-3}$)

G is the Shear modulus of sample. K is the Bulk modulus of sample.
The loss factor, defined as:

$$\text{Loss Factor} = \frac{\text{Rate of energy dissipation}}{2\pi F \times \text{Maximum stored energy}}$$

is obtained from:

$$\text{Loss Factor} = \frac{\alpha v}{\pi f}$$

where $\alpha$ is the attenuation in the sample. This is determined from the measured peak signal amplitude (i.e. peak stress p measured by the pickup crystal) by the relation:

$$\alpha = \frac{1}{d}\left\{ \log_e 2\beta^2) - \alpha_1(L-d) - \log_e\left[\sqrt{\frac{A^2 Q^2}{p^2} + 4\beta^2} - \frac{AQ}{p}\right]\right\}$$

where $$Q = \rho_1 v_1^2 \left\{\alpha_1^2 + \frac{4\pi^2 f^2}{v_1^2}\right\}^{\frac{1}{2}} \left\{(1+\beta^2)\cos^2 d\left(\frac{2\pi f}{v_1} - \frac{2\pi f}{v}\right) + (1-\beta^2)\sin^2 d\left(\frac{2\pi f}{v_1} - \frac{2\pi f}{v}\right)\right\}^{\frac{1}{2}}$$

A is a constant which is found from the initial test with no rubber sample present
L is the distance between the crystals (m)
$\rho_1$ is the density of the transmitting fluid (kg $m^{-3}$)
v is the signal velocity in the sample being tested $(ms^{-1})$

Having now described my invention, what I claim is:

1. Apparatus for determining elastic properties of materials comprising
a tank containing a fluid,
a first transducer for continuously generating stress waves,
a second transducer for detecting and receiving waves from said first transducer, said first and second transducers being aligned on a common axis
support means for detachably supporting a sample of material within said tank between said first and second transducers such that the surface of said sample is perpendicular to said common axis,
means for electrically exciting said first transducer at a frequency substantially lower than the resonant frequency of said first transducer, and
means for comparing properties of the waves generated by said first transducer and the waves received by said second transducer, at least one of said transducers being accurately adjustably locatable within said tank to detect a minimum (node) or maximum (antinode) of a standing wave set up in said tank.

2. Apparatus according to claim 1 wherein at least one of said transducers is moveable within said tank so as to vary the distance between said first and second transducers to avoid direct transmission of waves generated by said first transducer to said second transducer without passing through said sample, if present.

3. Apparatus according to claim 1 wherein said support means includes a pair of guides positioned on opposite sides of said tank so as to support a sample of material extending substantially across the width of the tank.

4. Apparatus according to claim 1 wherein said fluid has similar acoustic properties to the material to be tested.

5. Apparatus according to claim 1 wherein said means for comparing the wave properties includes a phase meter.

6. Apparatus according to claim 5 wherein said means further includes at least one A C voltmeter for measuring the amplitude of the signal received.

7. Apparatus according to claim 1 wherein said transducers are piezo electric crystal transducers.

8. Apparatus according to claim 1 wherein said tank comprises a plastics material.

9. A method of measuring the elastic properties of a material at two frequencies comprising the steps of:

(i) arranging first and second transducers in spaced relationship such that a continuous dilatational stress wave originating from the first transducer may be received by the second transducer;

(ii) adjusting the second transducer such that the signal received is a maximum;

(iii) positioning between said transducers a sample of the material to be tested;

(iv) comparing the stress wave received at the second transducer with that transmitted by the first transducer and calculating the elastic properties;

(v) repeating steps (i)–(iv) for a second frequency.

10. The method of claim 9 wherein said fourth step includes measuring the phase shift and the amplitude of said stress wave.

11. The method of claim 10 including a further step of calculating the elastic modulus of the material from said phase shift.

12. The method of claim 10 including a further step of calculating the loss factor of said material from said phase shift and said amplitudes.

* * * * *